(12) United States Patent
Takamori et al.

(10) Patent No.: US 6,884,902 B2
(45) Date of Patent: Apr. 26, 2005

(54) ORGANOMETALLIC IRIDIUM COMPOUND, PROCESS OF PRODUCING THE SAME, AND PROCESS OF PRODUCING THIN FILM

(75) Inventors: Mayumi Takamori, Sagamihara (JP); Noriaki Oshima, Yokohama (JP); Kazuhisa Kawano, Ebina (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 10/827,448

(22) Filed: Apr. 20, 2004

(65) Prior Publication Data

US 2004/0215029 A1 Oct. 28, 2004

(30) Foreign Application Priority Data

| Apr. 24, 2003 | (JP) | .................................. P. 2003-120109 |
| Apr. 24, 2003 | (JP) | .................................. P. 2003-120110 |
| Aug. 27, 2003 | (JP) | .................................. P. 2003-208975 |
| Dec. 18, 2003 | (JP) | .................................. P. 2003-420724 |
| Jan. 22, 2004 | (JP) | .................................. P. 2004-014454 |

(51) Int. Cl.$^7$ ............................. C07F 17/02; B05D 3/06; C23C 16/00
(52) U.S. Cl. ........................ 556/136; 427/252; 427/587
(58) Field of Search .......................... 556/136; 427/252, 427/587

(56) References Cited

U.S. PATENT DOCUMENTS 5,130,172 A 7/1992 Hicks et al.

FOREIGN PATENT DOCUMENTS

| JP | 11-292888 A | 10/1999 |
| WO | WO 91/01361 A | 2/1991 |

OTHER PUBLICATIONS

Fujisawa, et al., "Ir thin films for PZT capacitors prepared by MOCVD using a new Ir precursor", Materials Research Society Symposium Proceedings, vol. 784, 2004, pp. 269–274.

Kawano, et al., "A novel iridium precursor for MOCVD", Materials Research Society Symposium Proceedings, vol. 784, 2004, pp. 145–150.

(Continued)

Primary Examiner—Porfirio Nazario-Gonzalez
(74) Attorney, Agent, or Firm—Sughrue Mion, PLLC (57) ABSTRACT

An organometallic compound having a low melting point, excellent vaporization characteristic and low film formation temperature on a substrate, for forming an iridium-containing thin film by the CVD process is provided. The organometallic iridium compound is represented by the following general formula (1) or (2):

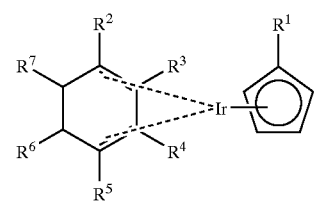

(1)

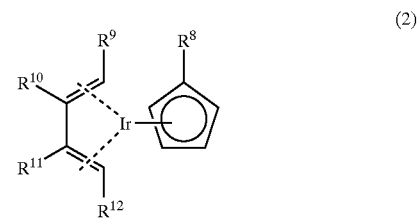

(2)

wherein $R^1$ represents hydrogen or a lower alkyl group; $R^2$ to $R^7$ each represents hydrogen, a halogen, or the like, provided that specific combinations of $R^1$ to $R^7$ are excluded; $R^8$ represents a lower alkyl group; $R^9$ to $R^{12}$ each represents hydrogen, a halogen, or the like, provided that specific combinations of $R^8$ to $R^{12}$ are excluded. Iridium-containing thin films are produced by using the compound as a precursor by CVD process.

8 Claims, 4 Drawing Sheets

OTHER PUBLICATIONS

Buchmann, et al., "Reactions with metal–coordinated olefins. Part VI. Trnasition metal NMR spectroscopy. Part X. Protonated diolefin complexes: model systems for carbon-hydrogen activation via metal complexation", Helvetica Chimica Acta, vol. 70, No. 6, 1987, pp. 1487–1506.

Green, et al., "Helium (He I) and helium(He II) photoelectron spectroscopic studies of the bonding in colbalt, rhodium and iridium cyclopentadienyl diene complexes", Organometallics, vol. 3, No. 2, Feb. 1984, pp. 211–217.

Powell, "Diene and dienyl complexes of transisition elements V. Preparation of .eta.–cyclopentadienyl–.eta.–methyl dienoaterhodium and –iridium complexes: base hydrolysis and protonation studies", Journal of Organometallic Chemistry, vol. 243, No. 2, Feb. 8, 1983, pp. 205–211.

Powell, "Diene and dienyl complexes of transition elements. III. Protonation of .eta.–cyclopentadienyl–.eta.–dienolrhodium and –iridium complexes: synthesis of cationic complexes containing open chain pentadienyl ligands", Journal of Organometallic Chemistry, vol. 206, No. 2, Feb. 24, 1981, pp. 239–255.

Powell, "Diene and dienyl complexes of transition elements. II. The protonation of .eta.–diaryldienone (.eta.–cyclopentadienyl)rhodium(I) and –iridium(I) complexes", Journal of Organometallic Chemistry, vol. 206, No. 2, Feb. 24, 1981, pp. 229–237.

Powell, ".eta.5–Cyclopentadienyl–.eta.5–syn–1–methlpenta-dienylrhodium and iridium cations—preparation and reactions with nucleophiles", Journal of Organometallic Chemistry, vol. 165, No. 3, Feb. 6, 1979, pp. C43–C46.

Powell, "Diene complexes of rhodium and iridium: preparation of complexes of the type 'M(diene)(C5H5)! using dienone and dienal ligands", Journal of Chemical Research, Synopses, No. 8, 1978, p. 283.

Johnson, et al., "Reactivity of coordinated ligands. XIII. Electrophilic substitution reactions of 1,3–cyclohexadiene complexes of rhodium (I) and iridium (I)", Journal of the Chemical Society, Dalton Transactions: Inorganic Chemistry, No. 19, 1972, pp. 2084–2089.

Winkhaus, et al., "Iridium(I)–Olefinkomplexe", Chemische Berichte, Verlag Chemie GMHB. Weinheim, DE, vol. 99, 1966, pp. 3610–3618.

Oro, "pi–Cyclopentadienyl (butadiene)iridium(I)", Inorganica Chimica Acta, vol. 21, 1977, p. L6.

Chapman and Hall, "Dictionary of Organometallic Compounds", vol. one, Ag–Mn, Iridium entry, pp. 1152–1197, 1984.

Wilkinson, et al., "Comprehensive Organometallic Chemistry, The Synthesis, Reactions and Structures of Organometallic Compounds", vol. 5, pp. 303–419, 1982.

Abel, et al., "Comprehensive Organometallic Chemistry II, A Review of the Literature 1982–1994", vol. 8, Cobalt, Rhodium, and Iridium, pp. 541–628, 1995.

Shimizu, et al., "MOCVD of Ir and $IrO_2$, Thin Films for PZT Capacitors", Materials Research Society Symp. Proc. vol. 655, pp. CC1.10.1–CC1.10.6, 2001.

Onderdelinden, et al., "Chloro– and Bromo–(alkene)iridium(I) Complexes", Inorganica Chimica Acta, vol. 6:3, pp. 420–426, Sep. 1972.

Winkhaus, et al., "Iridium(I)–Olefinkomplexe", Chem. Ber. vol. 99, pp. 3610–3618, 1966.

Oro, "π–Cyclopentadienyl(butadiene)iridium(I)", Inorganica Chimica Acta, 21 (1977) L6.

Müller, et al., "πOlefin–Iridium Komplexe, XIX *. Synthese, Struktur and Reaktivität von Bis(dien)iridium–benzyl–, cyclopropyl–, –vinyl– und –cyclopentadienyl–Komplexen", Journal of Organometallic Chemistry, 471 (1994) pp. 249–258.

Johnson, et al., "Reactivity of Co–ordinated Ligands. PartXIII. Electrophilic Substitution Reactions of Cyclohexa–1,3–diene Complexes of Rhodium(I) and Iridium(I)", J.C.S. Dalton, pp. 2084–2089 (1972).

Müller, et al., "π–Olefin–Iridium Komplexe IV. Umsetzungen von Chloro–Dien–Iridium–Verbindungen mit Lithiumorganylen ", Journal of Organometallic Chemistry, 191 (1980) 303–311.

Green, et al., "He I and He II Photoelectron Spectroscopic Studies of the Bonding in Cobalt, Rhodium, and Iridium Cyclopentadienyl Diene Complexes", Organometallics, 1984, 3, 211–217.

Moseley, et al., "Pentamethylcyclopentadienyl–rhodium and iridium Halides. Part III. Reactions with Cyclohexadienes", J. Chem. Soc., 1970, pp. 2884–2889.

Hoke, et al., "Low–temperature Vapour Deposition of High-purity Iridium Coatings from Cyclooctadiene Complexes of Iridium, Synthesis of a Novel Liquid Iridium Chemical Vapour Deposition Precursor", J. Mater. Chem., 1991, 1(4), 551–554.

Morozova, et al., "Thermal Properties of Ir(I) Precursors: Acetylacetonato(1,5– Cyclooctadiene) Iridium(I) and (Methylcyclopentadienyl)(1,5–Cyclooctadiene)Iridium(I)", Institute of Inorganic Chemistry of Siberian Branch of Russian Academy of Sciences.

Winkhaus, et al., "Iridium (I)–Diolefinkomplexe", Z. Naturforschg. 20b, 602–603 (1965).

Bezrukova, et al., Cyclohexa–1, 3–diene in Synthesis of $\eta^4$–diene, $\eta^5$–dienil and $\eta^6$ Arene derivatives of platinum metals, Nesmeyanova Institute of element–organic complexes, Academy of Science, USSR, pp. 2071–2076 (1986).

ORGANOMETALLIC IRIDIUM COMPOUND, PROCESS OF PRODUCING THE SAME, AND PROCESS OF PRODUCING THIN FILM

FIELD OF THE INVENTION

The present invention relates to an organometallic compound that can be a material for producing an iridium-containing thin film on a surface of a substrate.

DESCRIPTION OF THE RELATED ART

In recent years, in memory cells, for the sake of making it possible to realize higher integration and higher density, ferroelectric materials having a large relative dielectric constant are being eagerly investigated. Specifically, $Ta_2O_5$, BST ($(Ba, Sr)TiO_3$), and the like are investigated as a capacitor material. As electrode materials of these capacitors, noble metal thin films of ruthenium, platinum, iridium, and the like, or oxide thin films of these noble metals become necessary. In particular, iridium and iridium oxide are watched as a leading part of electrode materials in the future. As the production process of iridium and iridium oxide thin films, a sputtering process and a chemical vapor deposition process (CVD process) are employed. In particular, the CVD process is being considered as the main current in the production process of thin film electrodes in the future. This is because not only it is easy to produce uniform films, but also the step coverage is excellent, and therefore, this process can cope with higher density against the recent circuits and electronic parts.

As the precursor for forming thin films using this CVD process, it is considered that among metallic compounds, organometallic compounds that are low in melting point and easy in handling are suitable. Hitherto, tris(dipivaloylmethanato)iridium, tris(acetylacetonato)iridium, cyclopentadienyl(1,5-octadiene)iridium, and the like have been investigated as an organometallic compound for the purpose of depositing an iridium or iridium oxide thin film. These iridium compounds are high in stability in the atmosphere and non-toxic, and therefore, have aptitude as a precursor of CVD. However, these iridium compounds are solid at the ambient temperature and involve such a problem that vaporization of the precursor and transportation to a substrate are difficult.

In recent years, iridium compounds having a low melting point are being eagerly investigated. As a measure of making the organometallic iridium compounds have a low melting point, there is employed a compound in which at least one hydrogen atom on a cyclopentadiene ring is substituted with a lower alkyl group such as a methyl group and an ethyl group. For example, as cyclopentadien derivatives, ethylcyclopentadienyl(1,5-cyclooctadiene)iridium is disclosed (for example, JP-A-11-292888). Since this organometallic compound is liquid at the ambient temperature, and its melting point is low as compared with that of cyclopentadienyl(1,5-cyclooctadiene)iridium, it is considered that this compound is possessed of characteristics necessary as the precursor to be applied to the CVD process. However, this compound has extremely high stability, and the decomposition temperature of the complex is high. Accordingly, it is inevitably required to increase the substrate temperature at the time of film formation. Also, there is encountered such a problem that an iridium oxide film is hardly formed.

On the other hand, cyclopentadienyl(cyclohexadiene)iridium and cyclopentadienyl(butadiene)iridium are solid at the ambient temperature, too and therefore, involve problems in vaporization of the precursor and transportation to a substrate (for example, B. F. G. Johnson, J. Lewis, and D. J. Yarrow, *J. C. S. Dalton*, 2084 (1972) and L. A. ORO, *Inorg. Chem. Acta*, 21, L6 (1977)). There has not been made any report of synthesis of iridium complexes that are liquid at the ambient temperature and have excellent vaporization characteristic.

SUMMARY OF THE INVENTION

The present invention has been made in view of the above technical problems.

Accordingly, one object of the present invention is to provide an organometallic compound for forming a thin film comprising iridium or iridium oxide on a substrate by the CVD process, the organometallic compound having a low melting point, excellent vaporization characteristic and low film formation temperature.

Another object of the present invention is to provide a process of producing the organometallic compound.

Still another object of the present invention is to provide a process of producing an iridium-containing thin film using the organometallic compound The present inventors have made extensive and intensive investigations to overcome the above-described problems. As a result, it has been found that the decomposition temperature can be decreased by introducing a lower alkyl group into a cyclopentadiene derivative. The present inventors have further made extensive and intensive investigations to seek a novel iridium compound exhibiting a melting point such that it is liquid at the ambient temperature and having good vaporization characteristic and decomposition characteristic. As a result, they have reached the present invention.

The present invention provides an organometallic iridium compound represented by the following general formula (1):

(1)

wherein $R^1$ represents hydrogen or a lower alkyl group; and $R^2$, $R^3$, $R^4$, $R^5$, $R^6$, and $R^7$ are the same or different and each represents hydrogen, a halogen, a lower acyl group, a lower alkoxy group, a lower alkoxycarbonyl group, or a lower alkyl group, provided that the case where all of $R^1$, $R^2$, $R^3$, $R^4$, $R^5$, $R^6$, and $R^7$ represent hydrogen is excluded, or the following general formula (2):

(2)

wherein $R^8$ represents a lower alkyl group; and $R^9$, $R^{10}$, $R^{11}$, and $R^{12}$ are the same or different and each represents hydrogen, a halogen, a lower acyl group, a lower alkoxy group, a lower alkoxycarbonyl group, or a lower alkyl group, provided that the case where $R^8$, $R^9$, and $R^{11}$ each represents a methyl group, and $R^{10}$ and $R^{12}$ each represents hydrogen is excluded.

The present invention further provides a process of producing the organometallic iridium compound represented by the general formula (1), which comprises reacting an iridium compound, a cyclohexadiene derivative represented by the following general formula (3), and a cyclopentadiene derivative represented by following general formula (4):

(3)

(4)

wherein $R^1$, $R^2$, $R^3$, $R^4$, $R^5$, $R^6$, and $R^7$ are the same as defined above; and M represents an alkali metal.

The present invention further provides a process of producing the organometallic iridium compound represented by the general formula (2), which comprises reacting an iridium compound, a butadiene derivative represented by the following general formula (5), and a cyclopentadiene derivative represented by following general formula (6):

(5)

(6)

wherein $R^8$, $R^9$, $R^{10}$, $R^{11}$, and $R^{12}$ are the same as defined above; and M represents an alkali metal.

The present invention further provides a process of producing an iridium-containing thin film, which comprises using, as the precursor, the organometallic iridium compound represented by the general formula (1) or general formula (2).

IN THE DRAWINGS

1: Precursor container
2: Thermostat
3: Reaction chamber
4: Substrate
5: Oxidation gas
6: Counter gas
7: Carrier gas
8: Mass flow controller
9: Mass flow controller
10: Mass flow controller
11: Vacuum pump
12: Exhaust

DETAILED DESCRIPTION OF THE INVENTION

The present invention is described in detail below.

Definition of the terms used in the present specification and specific examples thereof will be described. The term "lower" as referred to in the present specification and claims means one containing a linear, branched or cyclic hydrocarbon group having 1–6 carbon atoms in the group given this term, unless otherwise indicated.

Therefore, examples of the lower alkyl group used in $R^1$ to $R^{12}$ include a methyl group, an ethyl group, an n-propyl group, an isopropyl group, an n-butyl group, an isobutyl group, a sec-butyl group, a tert-butyl group, a pentyl (amyl) group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclopropyl group, a cyclobutyl group, a cyclopentyl group, a cyclohexyl group, a cyclopropylmethyl group, a cyclopropylethyl group, and a cyclobutylmethyl group. Of those, a methyl group, an ethyl group, a propyl group, an isopropyl group, and a cyclopropyl group are preferable.

Examples of the lower alkoxy group used in $R^2$ to $R^7$ and $R^9$ to $R^{12}$ include a methoxy group, an ethoxy group, a propoxy group, an isopropoxy group, a butoxy group, an isobutoxy group, a sec-butoxy group, a tert-butoxy group, a pentyloxy group, a 1-methylbutyloxy group, a 2-methylbutyloxy group, a 3-methylbutyloxy group, a 1,2-dimethylpropyloxy group, a hexyloxy group, a 1-methylpentyloxy group, a 1-ethylpropyloxy group, a 2-methylpentyloxy group, a 3-methylpentyloxy group, a 4-methylpentyloxy group, a 1,2-dimethylbutyloxy group, a 1,3-dimethylbutyloxy group, a 2,3-dimethylbutyloxy group, a 1,1-dimethylbutyloxy group, a 2,2-dimethylbutyloxy group, and a 3,3-dimethylbutyloxy group. Of those, a methoxy group, an ethoxy group, and a propoxy group are preferable.

Examples of the lower alkoxycarbonyl group used in $R^2$ to $R^7$ and $R^9$ to $R^{12}$ include a methoxycarbonyl group, an ethoxycarbonyl group, a propoxycarbonyl group, an isopropoxycarbonyl group, a cyclopropoxycarbonyl group, a butoxycarbonyl group, an isobutoxycarbonyl group, a sec-butoxycarbonyl group, and a tert-butoxycarbonyl group. Of those, a methoxycarbonyl group, an ethoxycarbonyl group, a propoxycarbonyl group, an isopropoxycarbonyl group, and a cyclopropoxycarbonyl group are preferable.

Examples of the lower acyl group used in $R^2$ to $R^7$ and $R^9$ to $R^{12}$ include a formyl group, an acetyl group, a propionyl group, a butyryl group, an isobutyryl group, a valeryl group, a 1-methylpropylcarbonyl group, an isovaleryl group, a pentylcarbonyl group, a 1-methylbutylcarbonyl group, a 2-methylbutylcarbonyl group, a 3-methylbutylcarbonyl group, a 1-ethylpropylcarbonyl group, and a 2-ethylpropylcarbonyl group. Of those, a formyl group, an acetyl group, and a propionyl group are preferable.

In addition to the above lower alkyl group, lower alkoxy group, lower alkoxycarbonyl group and lower acyl group, a hydrogen atom or a halogen atom is preferably used for $R^2$ to $R^7$ and $R^9$ to $R^{12}$, which are the same or different. Specific examples of the halogen atom include fluorine, chlorine, bromine, and iodine. Of those, fluorine and chlorine are preferable.

Although examples of $R^1$ to $R^{12}$ are enumerated above, $R^8$ preferably represents an alkyl group having 1–3 carbon atoms; and $R^1$ to $R^7$ and $R^9$ to $R^{12}$ each preferably represents hydrogen or a lower alkyl group, and more preferably hydrogen or a lower alkyl group having 1–3 carbon atoms. Specific compounds represented by the general formula (1) include (ethylcyclopentadienyl)(1,3-cyclohexadiene)iridium and (methyl cyclopentadienyl)(1,3-cyclohexadiene)iridium; and specific compounds represented by the general formula (2) include (ethylcyclopentadienyl)(2,3-dimethyl-1,3-butadiene)iridium.

As described above, the iridium compound represented by the general formula (1) can be produced by reacting an iridium compound, a cyclohexadiene derivative represented by the general formula (3), and a cyclopentadiene derivative represented by the general formula (4); and the iridium compound represented the general formula (2) can be produced by reacting an iridium compound, a butadiene derivative represented by the general formula (5), and a cyclopentadiene derivative represented by the general formula (6).

Examples of the iridium compound used include inorganic iridium compounds and organometallic iridium compounds, especially iridium halides. Specific examples of the iridium compound include iridium(III) chloride hydrate, hexachloroiridic(IV) acid hydrate, hexachloroiridic(III) acid hydrate, sodium hexachloroiridate(III) hydrate, sodium hexachloroiridate(IV) hydrate, potassium hexachloroiridate(IV) hydrate, potassium hexachloroiridate(III) hydrate, iridium(III) bromide hydrate, potassium tris(oxalato)iridate(III) hydrate, ammonium hexachloroiridate(IV) hydrate, chloropentamineiridium(III) chloride hydrate, dichlorotetrakis(cyclooctene)diiridium, dichlorobis(1,5-cyclooctadiene)diiridium, dibromotetrakis(cyclooctene)diiridium, chlorotetrakis(ethylene)iridium, and dichlorotetrakis(ethylene)diiridium.

Of those, iridium(III) chloride hydrate, hexachloroiridic(IV) acid hydrate, sodium hexachloroiridate(IV) hydrate, ammonium hexachloroiridate(IV) hydrate, dichlorotetrakis(cyclooctene)diiridium, and dichlorotetrakis(ethylene)diiridium are preferable; and iridium(III) chloride hydrate, sodium hexachloroiridate(IV) hydrate, dichlorotetrakis(cyclooctene)diiridium, and dichlorotetrakis(ethylene)diiridium are more preferable.

In the general formula (4) and general formula (6), M represents an alkali metal. Examples of the alkali metal that can be used include lithium, sodium, and potassium. Of those, lithium and sodium are preferable. Of the cyclohexadiene derivatives represented by the general formula (3), the butadiene derivatives represented by the general formula (5), and the cyclopentadiene derivatives represented by the general formulae (4) and (6), those containing the above-described preferred $R^1$ to $R^{12}$ as substituents are preferable.

The order of reactions is not particularly limited, and the above compounds may be reacted successively or may be reacted at once. Preferably, a method can be used in which the iridium compound is reacted with the cyclohexadiene derivative represented by the general formula (3) or the butadiene derivative represented by the general formula (5), and the reaction product is then reacted with the cyclopentadiene derivative represented by the general formula (4) or (6). A post treatment is not particularly limited. However, as a general method, the reaction mixture after completion of the reaction is concentrated; the desired compound is extracted from the resulting mixture using an organic solvent such as pentane, hexane or ether; and the extract is subjected to column chromatography using alumina as a carrier and an appropriate organic solvent as an eluant, or the extract is subjected to distillation or sublimation under reduced pressure, whereby the desired iridium compound of the present invention can be obtained.

The production process of an iridium-containing thin film using the compound represented by the general formula (1) or (2) is not particularly limited, and any of the CVD process, the atomic layer deposition process (ALD process), and the spin coating process may be used. In the case of forming a film using the iridium compound represented by the general formula (1) or (2), the method of supplying the precursor to the substrate is not particularly limited. For example, any of the bubbling process and the liquid injection process may be used. In the case of producing a film by the CVD process or the ALD process, the organometallic iridium compound as the precursor is used alone or as mixtures of two or more thereof. The organometallic iridium compound may be used as it is, or may be dissolved in an organic solvent and then used as an organometallic iridium compound solution.

Examples of the organic solvent that can be used include alcohols (for example, methanol, ethanol, 1-propanol, isopropanol, and 1-butanol), esters (for example, ethyl acetate, butyl acetate, tertiary butyl acetate, and isoamyl acetate), glycol ethers (for example, ethylene glycol monoethyl ether, ethylene glycol monomethyl ether, and ethylene glycol monobutyl ether), ethers (for example, diethyl ether, glyme, diglyme, triglyme, tertiary butyl methyl ether, and tetrahydrofuran), ketones (for example, acetone, methyl butyl ketone, methyl isobutyl ketone, ethyl butyl ketone, dipropyl ketone, diisobutyl ketone, methyl amyl ketone, and cyclohexanone), and hydrocarbons (for example, pentane, hexane, cyclohexane, ethylcyclohexane, heptane, octane, benzene, toluene, and xylene). However, it should not be construed that the invention is limited thereto. For example, one or two or more kinds selected from these groups are used.

Most of the iridium compounds of the present invention are liquid at room temperature, and where such compounds are used as the CVD precursor, they can be quantitatively supplied by gas bubbling. Further, since these compounds can be thermally decomposed at low temperatures as compared with the conventional materials, it is possible to form an Ir-containing thin film having excellent step coverage on a substrate. In this way, it is possible to form an Ir-containing thin film from the iridium compound of the present invention by the CVD process having excellent mass productivity.

The present invention is described in more detail by reference to the Examples, but it should be understood that the invention is not construed as being limited thereto.

EXAMPLE 1

Synthesis and thermal decomposition characteristic of (ethylcyclopentadienyl)(1,3-cyclochexadiene)iridium Chlorobis(1,3-cyclohexadiene)iridium was synthesized by referring to G. Winkhaus and H. Singer, *Chem. Ber.*, 99, 3610 (1966). That is, 2.0 g of iridium chloride and 4.3 ml of cyclohexadiene were added to 30 ml of ethanol and 20 ml of water, and the mixture was allowed to react for 23 hours under refluxing conditions. After cooling, a deposit was filtered and then dried to obtain 1.6 g of chlorobis(1,3-cyclohexadiene)iridium.

0.5 g of chlorobis(1,3-cyclohexadiene)iridium was added to 10 ml of THF, and a reaction flask was cooled to −78° C., to which was then added 20 ml of a THF solution of 0.18 g of lithium ethylcyclopentadienide. The resulting mixture was stirred at −78° C. for 30 minutes, the temperature was then raised to room temperature step by step, and the resulting mixture was further allowed to react for 17.5 hours, followed by concentration to obtain a muddy mixture. The muddy mixture was subjected to extraction with hexane, and the extract solution was subjected to column chromatography (eluant: hexane) using alumina to obtain 145 mg of desired (ethylcyclopentadienyl)(1,3-cyclohexadiene)iridium represented by the following formula (7).

(7)

$^1$H-NMR (500 MHz, CDCl$_3$, δ ppm): 5.12 (t, J=2.0 Hz, 2H), 5.02 (t, J=2.0 Hz, 2H), 4.90 (m, 2H), 3.32 to 3.37 (m, 2H), 2.40 (q, J=7.5 Hz, 2H), 1.39 to 1.47 (m, 2H), 1.25 to 1.29 (m, 2H), 1.11 (t, J=7.5 Hz, 3H).

IR (neat, cm$^{-1}$): 810, 1000, 1170, 1315, 1460, 2925

MS (GC/MS, EI):

Molecular ion peak of (ethylcyclopentadienyl)(1,3-cyclohexadiene)iridium in terms of $^{193}$Ir: m/z 362

Orange Oily Material

Decomposition Characteristic

With respect to the resulting (ethylcyclopentadienyl)(1,3-cyclohexadiene)iridium, the thermal decomposition characteristic was examined in the following manner.

Analysis Condition of Decomposition Characteristic:

Analysis method: Power compensation differential scanning calorimetry (DSC)

Analysis condition:

Reference: Alumina

Inert gas: Nitrogen, 50 ml/min

Temperature rising: 10° C./min

Figure 1:
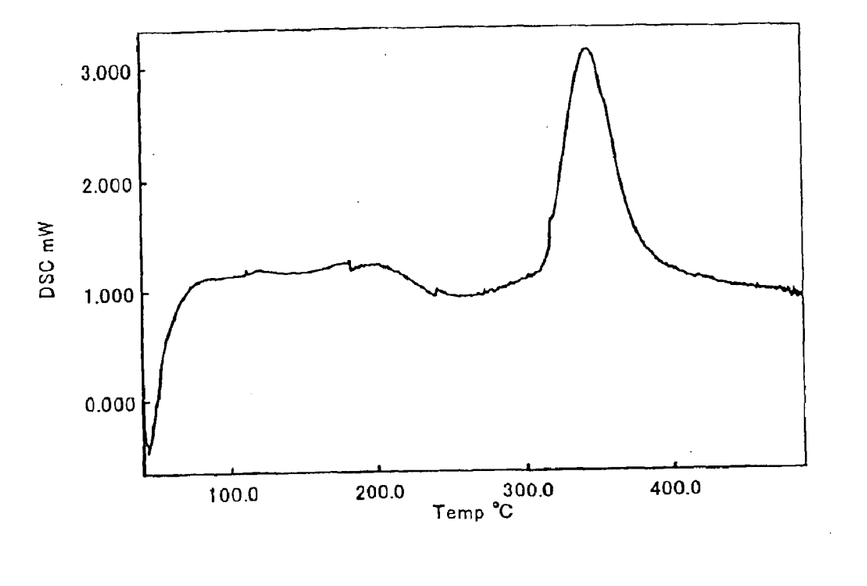
FIG. 1 is a view showing a DSC curve obtained in Example 1.

The results obtained are shown in FIG. 1. It is apparent from FIG. 1 that in the iridium compound of the present invention, the decomposition temperature is shifted to the low temperature side as compare with that in Comparative Example 1 described hereinafter.

COMPARATIVE EXAMPLE 1

Figure 2:
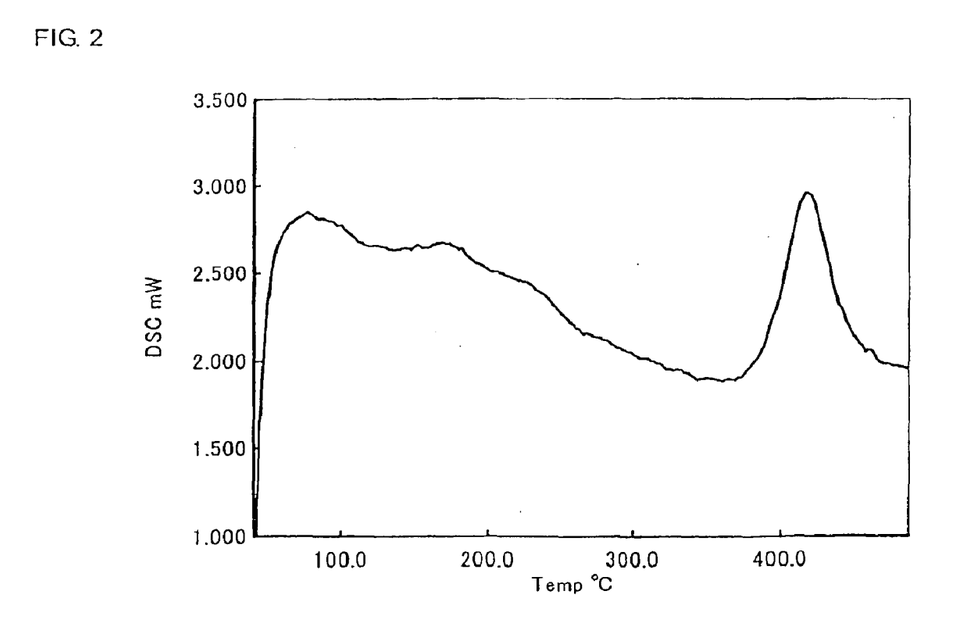
FIG. 2 is a view showing a DSC curve obtained in Comparative Example 1.

Decomposition characteristic of ethylcyclopentadienyl(1,5-cyclooctadiene)iridium With respect to ethylcyclopentadienyl(1,5-cyclooctadiene)iridium as a known compound, the decomposition characteristic was examined in the same manner as in Example 1. The results obtained are shown in FIG. 2. It is apparent from FIG. 2 that in this known compound, the decomposition temperature was located in the high temperature side as compared with those of the compounds of the present invention described in Examples 1 and 6.

EXAMPLE 2

Synthesis of (ethylcyclopentadienyl)(1,3-cyclohexadiene)iridium

Chlorobis(1,3-cyclohexadiene)iridium was obtained in the same manner as in Example 1. 0.9 g of chlorobis(1,3-cyclohexadiene)iridium was added to 15 ml of THF, and a reaction flask was cooled to −78° C., to which was then added 30 ml of a THF solution of 0.33 g of lithium ethylcyclopentadienide. The mixture was stirred at −78° C. for 30 minutes, the temperature was then raised to room temperature step by step, and the resulting mixture was further allowed to react for 1.5 hours, followed by concentration to obtain a muddy mixture. The muddy mixture was subjected to extraction with hexane, and the extract solution was subjected to distillation under reduced pressure to obtain 827 mg of desired (ethylcyclopentadienyl)(1,3-cyclohexadiene)iridium. It was confirmed that this compound was a desired compound by carrying out the $^1$H-NMR and MS analyses in the same manner as in Example 1.

EXAMPLE 3

Synthesis of (ethylcyclopentadienyl)(1,3-cyclohexadiene)iridium

Chlorobis(1,3-cyclohexadiene)iridium was obtained in the same manner as in Example 1. 7.8 g of chlorobis(1,3-cyclohexadiene)iridium was added to 60 ml of THF, and a reaction flask was cooled to −78° C., to which was then added 100 ml of a THF solution of 2.5 g of sodium ethylcyclopentadienide. The mixture was stirred at −78° C. for 30 minutes, the temperature was then raised to room temperature step by step, and the resulting mixture was further allowed to react for one hour, followed by concentration to obtain a muddy mixture. The muddy mixture was subjected to extraction with hexane, and the extract solution was subjected to distillation under reduced pressure to obtain 4.9 g of desired (ethylcyclopentadienyl)(1,3-cyclohexadiene)iridium. It was confirmed that this compound was a desired compound by carrying out the ¹H-NMR and MS analyses in the same manner as in Example 1.

EXAMPLE 4

Synthesis of (methylcyclopentadienyl)(1,3-cyclohexadiene)iridium

Chlorobis(1,3-cyclohexadiene)iridium was obtained in the same manner as in Example 1. 1.2 g of chlorobis(1,3-cyclohexadiene)iridium was added to 20 ml of THF, and a reaction flask was cooled to −78° C., to which was then added 40 ml of a THF solution of 0.26 g of lithium methylcyclopentadienide. After completion of the addition, the temperature was raised to room temperature step by step, and the resulting mixture was allowed to react for one hour, followed by concentration to obtain a muddy mixture. The muddy mixture was subjected to extraction with hexane, and the extract solution was subjected to sublimation under reduced pressure to obtain 101 mg g of desired (methylcyclopentadienyl)(1,3-cyclohexadiene)iridium represented by the following formula (8).

(8)

¹H-NMR (500 MHz, Benzene-d6, δ ppm): 4.98 (t, J=2.0 Hz, 2H), 4.93 to 4.97 (m, 2H), 4.87 (t, J=2.0 Hz, 2H), 3.42 to 3.47 (m, 2H), 1.98 (s, 3H), 1.67 to 1.74 (m, 2H), 1.48 to 1.54 (m, 2H).

MS (GC/MS, EI):

Molecular ion peak of (methylcyclopentadienyl)(1,3-cyclohexadiene)iridium in terms of ¹⁹³Ir: m/z 352

White Needle Crystal

EXAMPLE 5

X-Ray diffraction of (methylcyclopentadienyl)(1,3-cyclohexadiene)iridium

Figure 3:
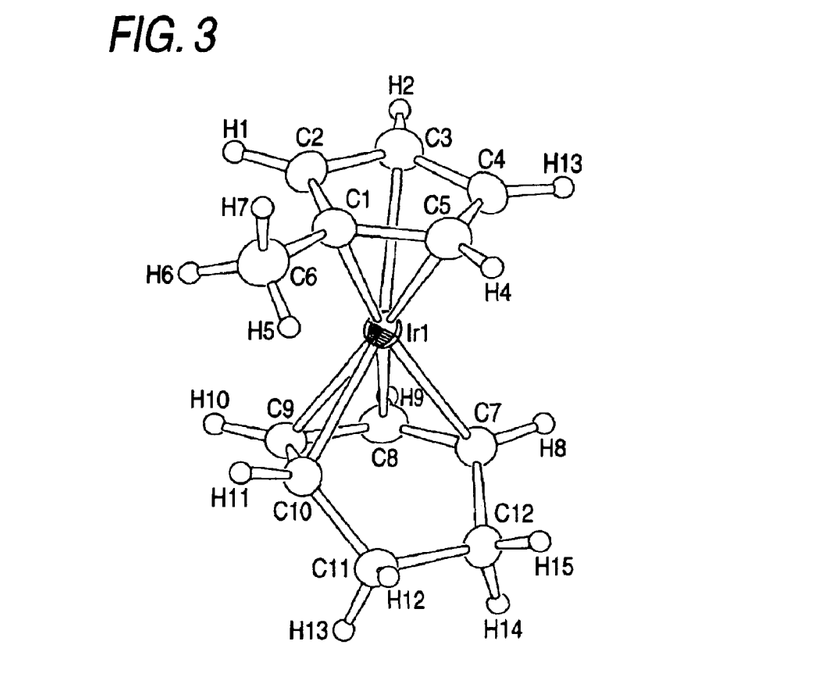
FIG. 3 is a view showing X-ray diffraction obtained in Example 5.

With respect to (methylcyclopentadienyl)(1,3-cyclohexadiene)iridium obtained in Example 4, the X-ray diffraction was carried out. The results obtained are shown in FIG. 3.

EXAMPLE 6

Synthesis and thermal decomposition characteristic of (ethylcyclopentadienyl)(2,3-dimethyl-1,3-butadiene)iridium Chlorobis(2,3-dimethyl-1,3-butadiene)iridium was synthesized by referring to G. Winkhaus and H. Singer, *Chem. Ber.*, 99, 3610 (1966). That is, 1.7 g of sodium hexachloroiridate(IV) hexahydrate and 2.7 ml of 2,3-dimethyl-1,3-butadiene were added to 20 ml of ethanol and 10 ml of water, and the mixture was allowed to react under heating at 40° C. for 23 hours. After cooling, a deposit was filtered and then dried to obtain 283 mg of chlorobis(2,3-dimethyl-1,3-butadiene)iridium.

0.28 g of chlorobis(2,3-dimethyl-1,3-butadiene)iridium was added to 7 ml of THF, and a reaction flask was cooled to −78° C., to which was then added 15 ml of a THF solution of 0.17 g of lithium ethylcyclopentadienide. The mixture was stirred at −78° C. for 5 minutes, the temperature was then raised to room temperature step by step, and the resulting mixture was further allowed to react for 1.5 hours, followed by concentration to obtain a muddy mixture. The muddy mixture was subjected to extraction with hexane, and the extract solution was subjected to column chromatography (eluant: hexane) using alumina to obtain 159 mg of desired (ethylcyclopentadienyl)(2,3-dimethyl-1,3-butadiene)iridium represented by the following formula (9).

(9)

¹H-NMR (500 MHz, CDCl₃, δ ppm): 5.01 (t, J=2.0 Hz, 2H), 4.97 (t, J=2.0 Hz, 2H), 2.43 (d, J=1.5 Hz, 2H), 2.36 (q, J=7.5 Hz, 2H), 3.16(s, 6H), 1.11 (t, J=7.5 Hz, 3H), −0.05 (d, J=1.5 Hz, 2H).

IR (neat, cm⁻¹): 810, 1035, 1375, 1450, 2970

MS (GC/MS, EI):

Molecular ion peak of (2,3-dimethyl-1,3-butadiene)(ethylcyclopentadienyl)iridium in terms of ¹⁹³Ir: m/z 365

Orange Oily Material

Decomposition Characteristic

With respect to the resulting (ethylcyclopentadienyl)(2,3-dimethyl-1,3-butadiene)iridium, the thermal decomposition characteristic was examined in the following manner.

Analysis condition of decomposition characteristic:

Analysis method: Input compensation differential scanning calorimetry (DSC)

Analysis condition:

Reference: Alumina

Inert gas: Nitrogen, 50 ml/min

Temperature rising: 10° C./min

Figure 4:
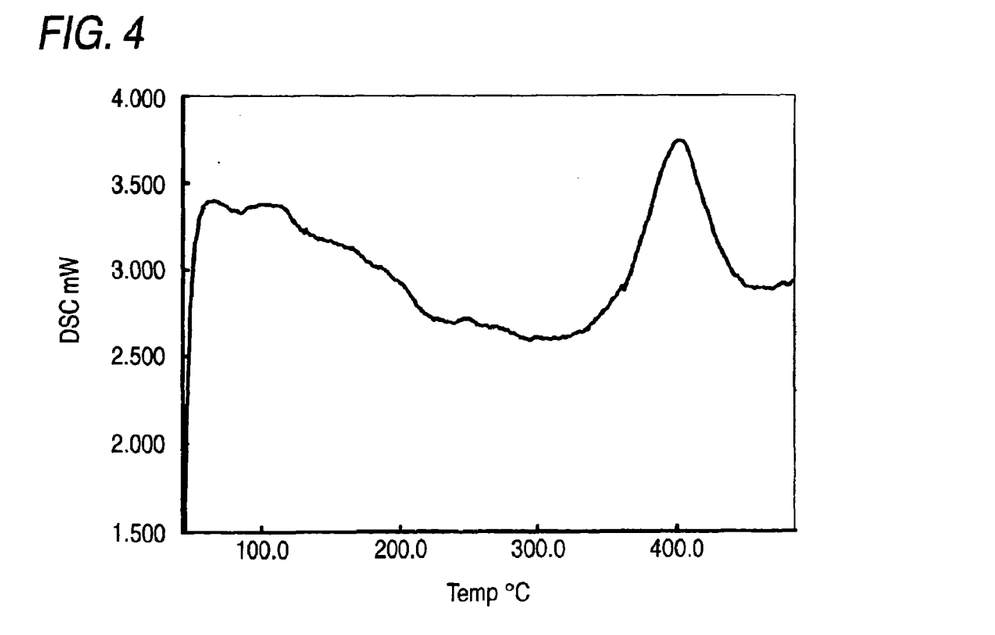
FIG. 4 is a view showing a DSC curve obtained in Example 6.

The results obtained are shown in FIG. 4. It is apparent from FIG. 4 that in the iridium compound of the present invention, the decomposition temperature is shifted to the low temperature side as compare with that in Comparative Example 1 described above.

EXAMPLE 7

Figure 5:
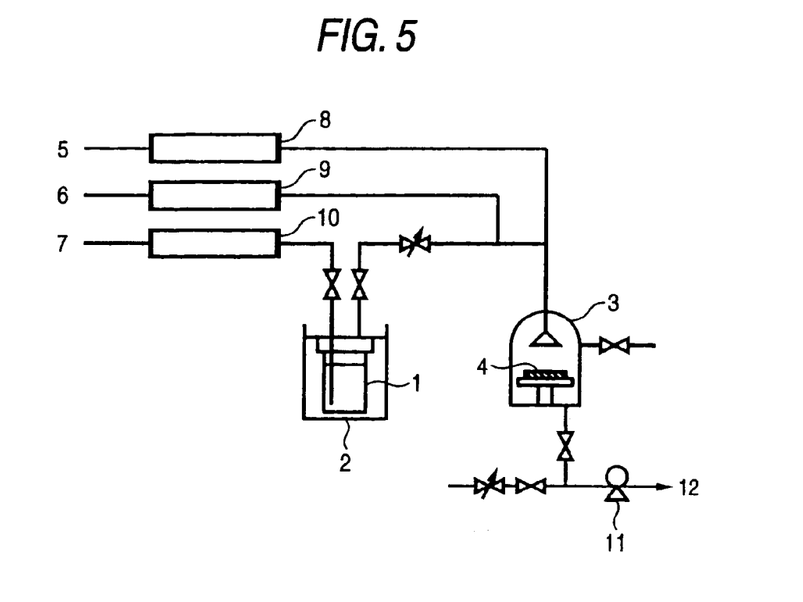
FIG. 5 is a schematic view of a device of the CVD process used in Examples 7 and 8.
Figure 6:
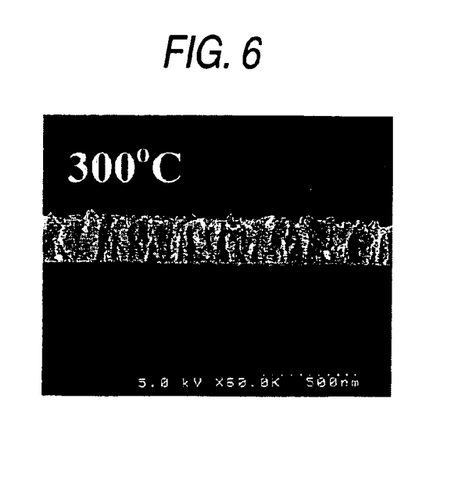
FIG. 6 is a view showing an SEM image of an Ir-containing thin film formed at 300° C. in Example 7.
Figure 7:
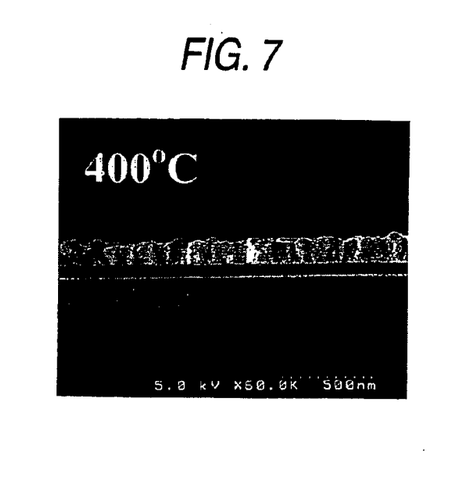
FIG. 7 is a view showing an SEM image of an Ir-containing thin film formed at 400° C. in Example 7.
Figure 8:
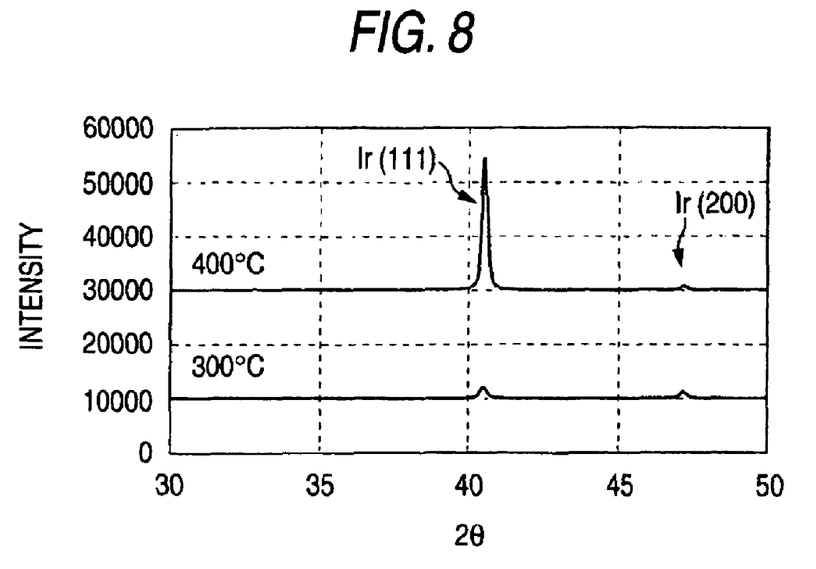
FIG. 8 is a view showing an X-ray diffraction diagram obtained in Example 7.

Production of iridium-containing thin film using (ethylcyclopentadienyl)(1,3-cyclohexadiene)iridium as the precursor by the CVD process A device shown in FIG. 5 was used, and an Si substrate in which an SiO₂ film of 100 nm had been formed on the surface thereof was used as a substrate 4. 10 g of (ethylcyclopentadienyl)(1,3-cyclohexadiene)iridium was charged into a precursor container 1 and made constant at 80° C. upon heating on an oil bath 2. Using a vacuum pump 11 and pressure control valves, a reaction chamber 3 was adjusted at 8 Torr, and the precursor container 1 was adjusted at 100 Torr, respectively. Nitrogen was used as a carrier gas 7, and its flow rate was set up at 100 sccm by a mass flow controller 10. Oxygen was used as an oxidation gas 5, and nitrogen was used as a counter gas 6. The flow rate of the oxidation gas was set up at 4 sccm by a mass flow controller 8, and the sum of the flow rate of the counter gas and the flow rate of the oxidation gas was set up at 100 sccm. The substrate 4 was set up at 300° C. and 400° C., respectively, and subjected to film formation for 55 minutes while maintaining the heated state. FIGS. 6 and 7 show SEM images of Ir-containing thin films each formed on the substrate at 300° C. and 400° C., respectively. X-ray diffraction diagrams of these films are shown in FIG. 8. In any case, an Ir thin film was obtained.

EXAMPLE 8

Figure 9:
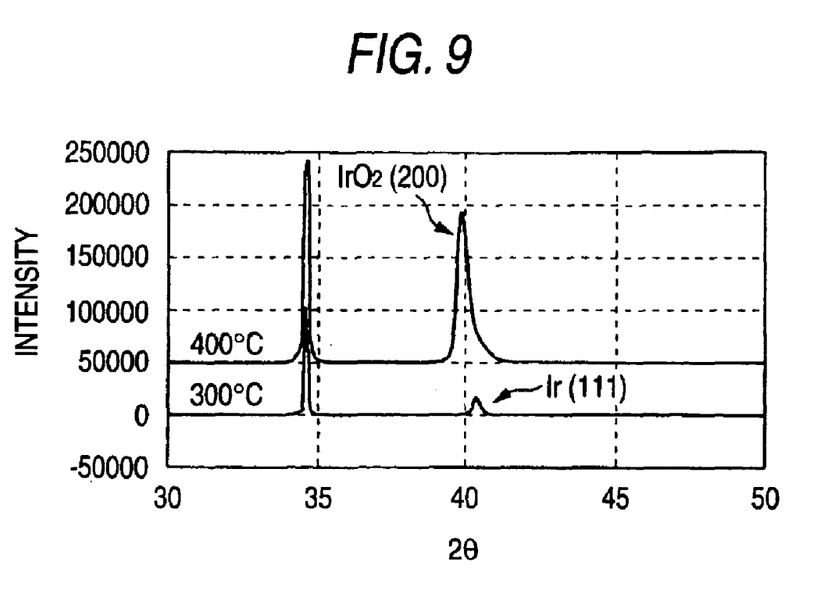
FIG. 9 is a view showing an X-ray diffraction diagram obtained in Example 8.

Production of iridium-containing thin film using (ethylcyclopentadienyl)(1,3-cyclohexadiene)iridium as the precursor by the CVD process A device shown in FIG. 5 was used, and a YSZ (yttria-stabilized zirconia) substrate was used as a substrate 4. 10 g of (ethylcyclopentadienyl)(1,3-cyclohexadiene)iridium was charged into a precursor container 1 and made constant at 80° C. upon heating on an oil bath 2. Using a vacuum pump 11 and pressure control valves, a reaction chamber 3 was adjusted at 8 Torr, and the precursor container 1 was adjusted at 100 Torr, respectively. Nitrogen was used as a carrier gas 7, and its flow rate was set up at 100 sccm by a mass flow controller 10. Oxygen was used as an oxidizing gas 5, and nitrogen was used as a counter gas 6. The flow rate of the oxidation gas was set up at 4 sccm by a mass flow controller 8, and the sum of the flow rate of the counter gas and the flow rate of the oxidation gas was set up at 100 sccm. The substrate 4 was set up at 300° C. and 400° C., respectively, and subjected to film formation for 55 minutes while keeping the heated state. X-ray diffraction diagrams of these films are shown in FIG. 9. In the case where the substrate temperature was 300° C., an Ir thin film was obtained, and in the case where the substrate temperature was 400° C., an iridium oxide thin film was obtained.

It should further be apparent to those skilled in the art that various changes in form and detail of the invention as shown and described above may be made. It is intended that such changes be included within the spirit and scope of the claims appended hereto.

What is claimed is:

1. An organometallic iridium compound represented by the following formula (1):

(1)

wherein $R^1$ represents hydrogen or a lower alkyl group; and $R^2$, $R^3$, $R^4$, $R^5$, $R^6$, and $R^7$ are the same or different and each represents hydrogen, a halogen, a lower acyl group, a lower alkoxy group, a lower alkoxycarbonyl group, or a lower alkyl group, provided that the case where all of $R^1$, $R^2$, $R^3$, $R^4$, $R^5$, $R^6$, and $R^7$ represent hydrogen is excluded.

2. An organometallic iridium compound represented by the following general formula (2):

(2)

wherein $R^8$ represents a lower alkyl group; and $R^9$, $R^{10}$, $R^{11}$, and $R^{12}$ are the same or different and each represents hydrogen, a halogen, a lower acyl group, a lower alkoxy group, a lower alkoxycarbonyl group, or a lower alkyl group, provided that the case where $R^8$, $R^9$, and $R^{11}$ each represents a methyl group, and $R^{10}$ and $R^{12}$ each represents hydrogen is excluded.

3. A process of producing an organometallic iridium compound represented by the following general formula (1), which comprises reacting an iridium compound, a cyclohexadiene derivative represented by the following general formula (3), and a cyclopentadiene derivative represented by following general formula (4):

(1)

(3)

(4)

wherein $R^1$ represents hydrogen or a lower alkyl group; $R^2$, $R^3$, $R^4$, $R^5$, $R^6$, and $R^7$ are the same or different and each represents hydrogen, a halogen, a lower acyl group, a lower alkoxy group, a lower alkoxycarbonyl group, or a lower alkyl group, provided that the case where all of $R^1$, $R^2$, $R^3$, $R^4$, $R^5$, $R^6$, and $R^7$ represent hydrogen is excluded; and M represents an alkali metal.

4. A process of producing an organometallic iridium compound represented by the following general formula (2), which comprises reacting an iridium compound, a butadiene derivative represented by the following general formula (5), and a cyclopentadiene derivative represented by following general formula (6):

(2)

(1)

wherein $R^1$ represents hydrogen or a lower alkyl group; and $R^2$, $R^3$, $R^4$, $R^5$, $R^6$, and $R^7$ are the same or different and each represents hydrogen, a halogen, a lower acyl group, a lower alkoxy group, a lower alkoxycarbonyl group, or a lower alkyl group, provided that the case where all of $R^1$, $R^2$, $R^3$, $R^4$, $R^5$, $R^6$, and $R^7$ represent hydrogen is excluded.

6. A process of producing an iridium-containing thin film, which comprises using, as a precursor, an organometallic iridium compound represented by the following general formula (2):

(5)

(2)

wherein $R^8$ represents a lower alkyl group; and $R^9$, $R^{10}$, $R^{11}$, and $R^{12}$ are the same or different and each represents hydrogen, a halogen, a lower acyl group, a lower alkoxy group, a lower alkoxycarbonyl group, or a lower alkyl group, provided that the case where $R^8$, $R^9$, and $R^{11}$ each represents a methyl group, and $R^{10}$ and $R^{12}$ each represents hydrogen is excluded.

7. The process as claimed in claim 5, which comprises using the CVD process.

8. The process as claimed in claim 6, which comprises using the CVD process.

(6)

wherein $R^8$ represents a lower alkyl group; $R^9$, $R^{10}$, $R^{11}$, and $R^{12}$ are the same or different and each represents hydrogen, a halogen, a lower acyl group, a lower alkoxy group, a lower alkoxycarbonyl group, or a lower alkyl group, provided that the case where $R^8$, $R^9$, and $R^{11}$ each represents a methyl group, and $R^{10}$ and $R^{12}$ each represents hydrogen is excluded; and M represents an alkali metal.

5. A process of producing an iridium-containing thin film, which comprises using, as a precursor, an organometallic iridium compound represented by the following general formula (1):

* * * * *